United States Patent
Collazo et al.

(10) Patent No.: US 7,390,327 B2
(45) Date of Patent: Jun. 24, 2008

(54) PUNCH APPARATUS AND METHOD FOR SURGERY

(75) Inventors: Carlos E. Collazo, Old Greenwich, CT (US); Scott Logan, Ringwood, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 243 days.

(21) Appl. No.: 10/678,351

(22) Filed: Oct. 3, 2003

(65) Prior Publication Data

US 2005/0075640 A1    Apr. 7, 2005

(51) Int. Cl.
   *A61F 5/00* (2006.01)
(52) U.S. Cl. .......................................... 606/86
(58) Field of Classification Search ................... 606/53, 606/86–87, 99–100, 102, 105
   See application file for complete search history.

(56) References Cited

U.S. PATENT DOCUMENTS

| | | | | |
|---|---|---|---|---|
| 43,909 A | * | 8/1864 | Hair | ............................ 606/175 |
| 4,416,278 A | * | 11/1983 | Miller | ......................... 606/174 |
| 4,626,425 A | * | 12/1986 | Scheithauer et al. | ... 423/594.13 |
| 5,282,866 A | * | 2/1994 | Cohen et al. | ............. 623/20.34 |
| 5,443,471 A | * | 8/1995 | Swajger | ......................... 606/99 |
| 5,534,006 A | * | 7/1996 | Szabo et al. | .................. 606/100 |
| 5,634,927 A | * | 6/1997 | Houston et al. | ................ 606/96 |
| 5,683,469 A | * | 11/1997 | Johnson et al. | ........... 623/20.32 |
| 5,690,636 A | * | 11/1997 | Wildgoose et al. | ............. 606/88 |
| 5,788,701 A | | 8/1998 | McCue | |
| 5,951,603 A | | 9/1999 | O'Neil et al. | |
| 5,976,147 A | | 11/1999 | LaSalle et al. | |
| 6,059,788 A | | 5/2000 | Katz | |
| 6,063,091 A | | 5/2000 | Lombardo et al. | |
| 6,063,123 A | | 5/2000 | Burrows et al. | |
| 6,159,216 A | * | 12/2000 | Burkinshaw et al. | ........... 606/88 |
| 6,193,723 B1 | | 2/2001 | Cripe et al. | |
| 6,228,091 B1 | | 5/2001 | Lombardo et al. | |
| 6,355,045 B1 | * | 3/2002 | Gundlapalli et al. | ........... 606/88 |
| 6,506,216 B1 | | 1/2003 | McCue et al. | |
| 6,520,966 B1 | | 2/2003 | Kohler et al. | |
| 6,626,913 B1 | * | 9/2003 | McKinnon et al. | ............. 606/99 |

* cited by examiner

*Primary Examiner*—Eduardo C. Robert
*Assistant Examiner*—James L Swiger
(74) *Attorney, Agent, or Firm*—Lerner, David, Littenberg, Krumholz & Mentlik., LLP

(57) ABSTRACT

A bone implantation instrument, punch apparatus and method of forming a recess in a bone are described. The instrument and apparatus include a punch that is extracted from the bone by prying force.

11 Claims, 9 Drawing Sheets

PUNCH APPARATUS AND METHOD FOR SURGERY

FIELD OF THE INVENTION

The invention relates to methods and tools used in surgery. More particularly, the invention relates to a punch apparatus used during knee surgery and a method of using the apparatus.

BACKGROUND OF THE INVENTION

Total knee arthroplasty typically involves the replacement of a portion of the patella, femur and/or tibia with artificial components. In many surgeries, a proximal portion of the tibia and a distal portion of the femur are resected, prepared by further cutting, shaping, reaming, and/or punching the bone and replaced with artificial components. As used herein, when referring to bones or other body parts, the term "proximal" means closest to the heart and the term "distal" means more distant from the heart.

After preparing the distal surface of the femur and the proximal surface of the tibia, an opening is made into the medullary canal of the femur, and an opening is made into the medullary canal of tibia. Some implant components include an intramedullary (IM) stem, and when these components are used, the interior surface of the medullary canal and the IM tem of the femoral component are usually covered with polymeric cement. The IM stem is inserted into the medullary canal of the femur until the interior surface of the femoral component meets the distal surface of the femur. The IM stem of the tibial component is usually similarly cemented and inserted in the medullary canal of the tibia.

Occasionally, the femoral and tibial components are press fit without the use of cement. The use of cement has advantages and disadvantages. Press fit components rely on bone quality to obtain good fixation. Sometimes, however, it is impossible to obtain good fixation with a press fit component, and sometimes a press fit component will fail early because of failure of successful biological ingrowth. Cement assures good fixation, but may put strain along the component stem. In addition, cement can complicate the removal of a failed component.

Often, due to normal wear over time, the prosthetic knee must be replaced via a procedure known as revision surgery. When the primary cemented prosthetic is removed, the proximal surface of the tibia and the distal surface of the femur typically exhibit cavernous defects. Absent the use of bone graft, the proximal surface of the tibia and the distal surface of the femur must be carefully resected to remove cavernous defects before a replacement knee can be installed.

In addition, a revision surgery typically requires broaching and/or reaming the intramedullary (IM) canals to remove any remaining cement or cavernous defects existing in the canals before a replacement knee can be installed. Removal of the femoral component and preparation of the distal femur is performed using techniques known in the art. According to the state of the art, after the primary prosthetic is removed, the proximal tibia is resected with a cutting guide. The medullary canal is reamed. A proximal resection guide is attached to the reamer, and proximal resection is completed via slots in the guide.

Defects in the tibia, if present, are evaluated. If a tibial implant augment is deemed necessary, the proximal tibia is further prepared by attaching a multi-slotted augment cutting guide to the reamer and resecting the bone through the slot representing the optimum thickness for the augment to be implanted. After resection of the proximal tibia is completed, the tibial plateau is sized by placing and positioning the tibial template that provides the best coverage for that given tibia. The tibial template is pinned in this position. A punch guide is attached to the template and a keel or fin punch is used to provide a keeled or finned opening to accept the implant. The tibia implant has a cross-sectional keel or fin shape corresponding to the opening punched in the tibia that prevents rotation of the implant once it has been inserted into the punched opening.

Removal of the keel or fin punch typically involves the use of a slap hammer. Examples of devices that utilize slap hammers for the removal of punch instruments during knee surgery are disclosed in U.S. Pat. Nos. 5,690,636 and 5,788,701. Use of a slap hammer to remove a punch has certain disadvantages. One disadvantage of using a slap hammer is that the punch is removed in an uncontrolled manner. In addition, attachment and use of the slap hammer during a surgical procedure is relatively time-consuming, considering the relatively short time period to complete the surgical procedure. It would be desirable to provide a device and method that provides for the controlled removal of a punch from a bone during knee surgery.

SUMMARY OF THE INVENTION

In accordance with one or more embodiments of the present invention, a bone implantation instrument is provided. The bone implantation instrument can be used in knee surgeries and other types of surgeries in which it a punch is inserted into a bone and must later be removed from the bone. The instrument comprises a punch having a proximal portion and a distal portion defining a longitudinal axis and a pivot between the proximal portion and distal portion. The pivot permits the proximal portion to be rotated about the pivot and to be moved at an angle with respect to the longitudinal axis. The distal portion of the punch is configured to be advanced into a bone. According to one or more embodiments, the instrument includes a fulcrum configured to cooperate with the proximal portion when the proximal portion is rotated about the pivot to extract the distal portion from the bone. The fulcrum may include a raised surface adjacent the guide.

In certain embodiments, the instrument includes a guide member configured to guide the distal portion of the punch into the bone. In preferred embodiments, the pivot comprises a slot associated with the proximal portion and a pin associated with the distal portion of the punch. Preferably, the slot is elongated and includes an advancement position and retraction position.

According to some embodiments, the punch includes a locking member to prevent rotation of the proximal portion as the punch is advanced into the bone. In certain embodiments, the guide includes an engagement element for securing the guide to a punch template associated with the bone. The guide may also include a handle. According to one or more embodiments, the distal portion of the punch is generally keel-shaped in cross section.

Other embodiments relate to a bone implantation instrument comprising a punch having a distal end and a proximal end and a longitudinal axis, a guide for directing the punch into a bone during advancement of the punch, and a lever for extracting the punch from the bone. In certain embodiments, the lever includes a portion of the punch and a fulcrum associated with the guide.

Still another embodiment of the invention relates to a punch comprising a generally keel-shaped distal end and a proximal end defining a longitudinal axis, wherein the punch is pivotal along a portion of the longitudinal axis. The punch is configured to be extracted from a bone by prying force exerted adjacent a pivot along the longitudinal axis.

Other embodiments relate to a method of extracting a punch from a bone during a knee arthroplasty comprising prying the punch from the bone. According to the method, preferably the punch has a proximal portion, a distal portion and longitudinal axis, and prying force is provided by applying force to the proximal portion of the punch.

Another embodiment relates to a method of extracting a punch from a bone during a surgery such as a knee arthroplasty comprising providing a punch having handle portion, an impaction tip, a longitudinal axis and a pivot along the longitudinal axis and rotating the handle about the pivot to extract the punch from the bone. In certain embodiments, a portion of the handle is supported by a fulcrum during extraction of the punch from the bone.

Still another embodiment relates to a method of forming a recess in a bone, comprising driving a punch having a handle portion, a tip and a longitudinal axis through a guide and into a bone, and extracting the punch from the bone using a lever formed by a portion of the punch. In certain embodiments, the bone is a tibia.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION OF EXEMPLARY EMBODIMENTS

Figure 1:
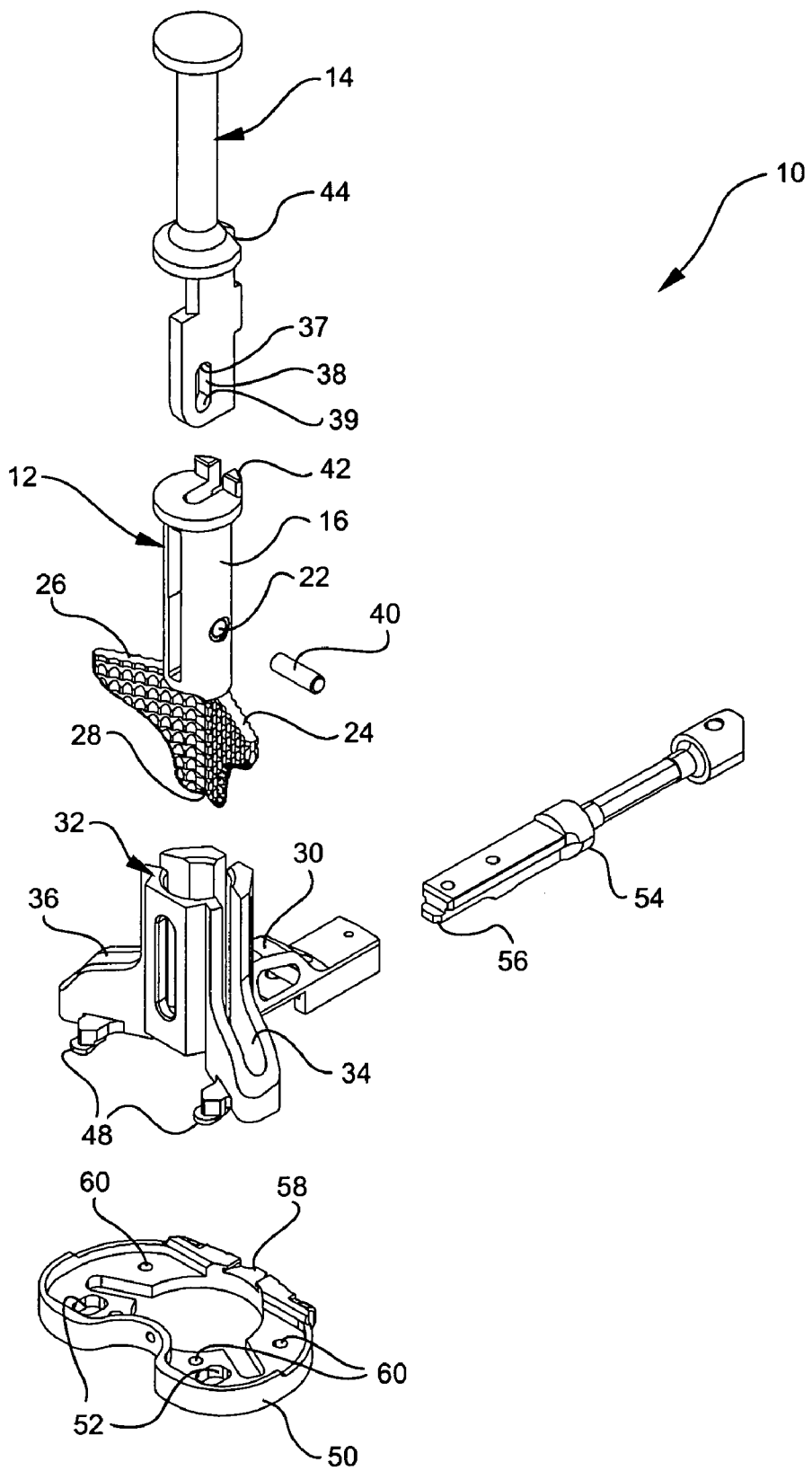
FIG. 1 is an exploded perspective view of the bone implantation apparatus according to one embodiment.
Figure 2:
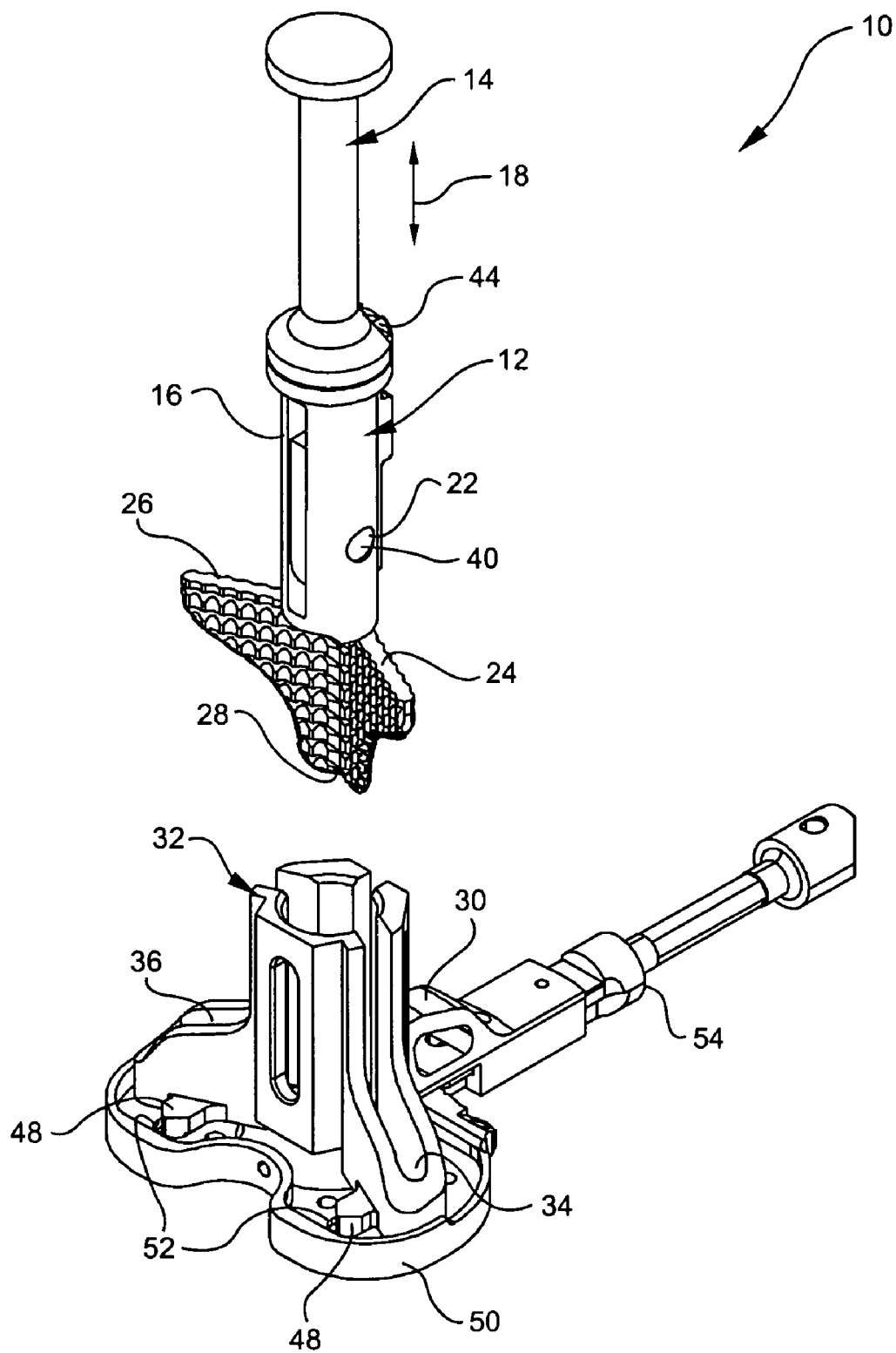
FIG. 2 is a perspective view of the bone implantation apparatus prior to insertion of the punch in the guide according to one embodiment.
Figure 3:
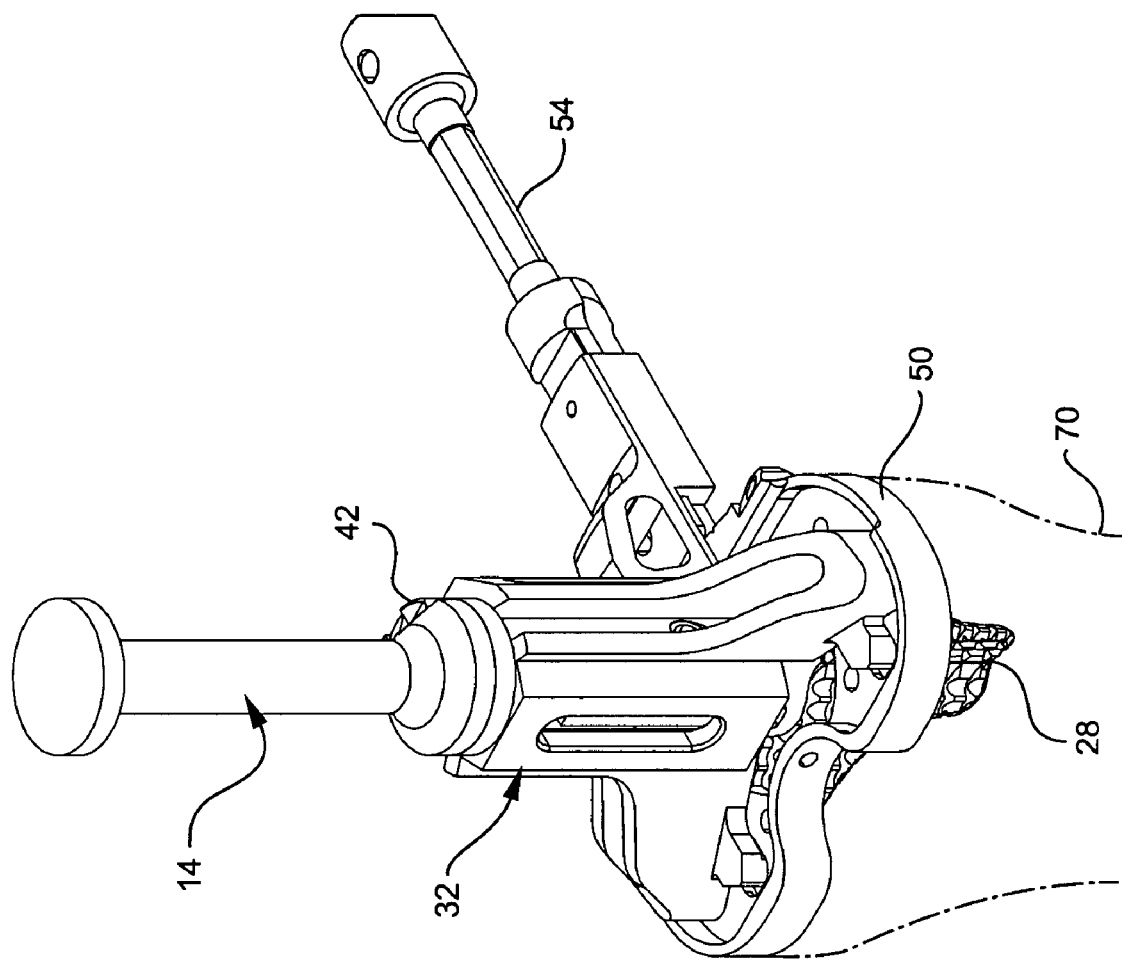
FIG. 3 is an assembled perspective view of a bone implantation instrument according to one embodiment of the invention.
Figure 4:
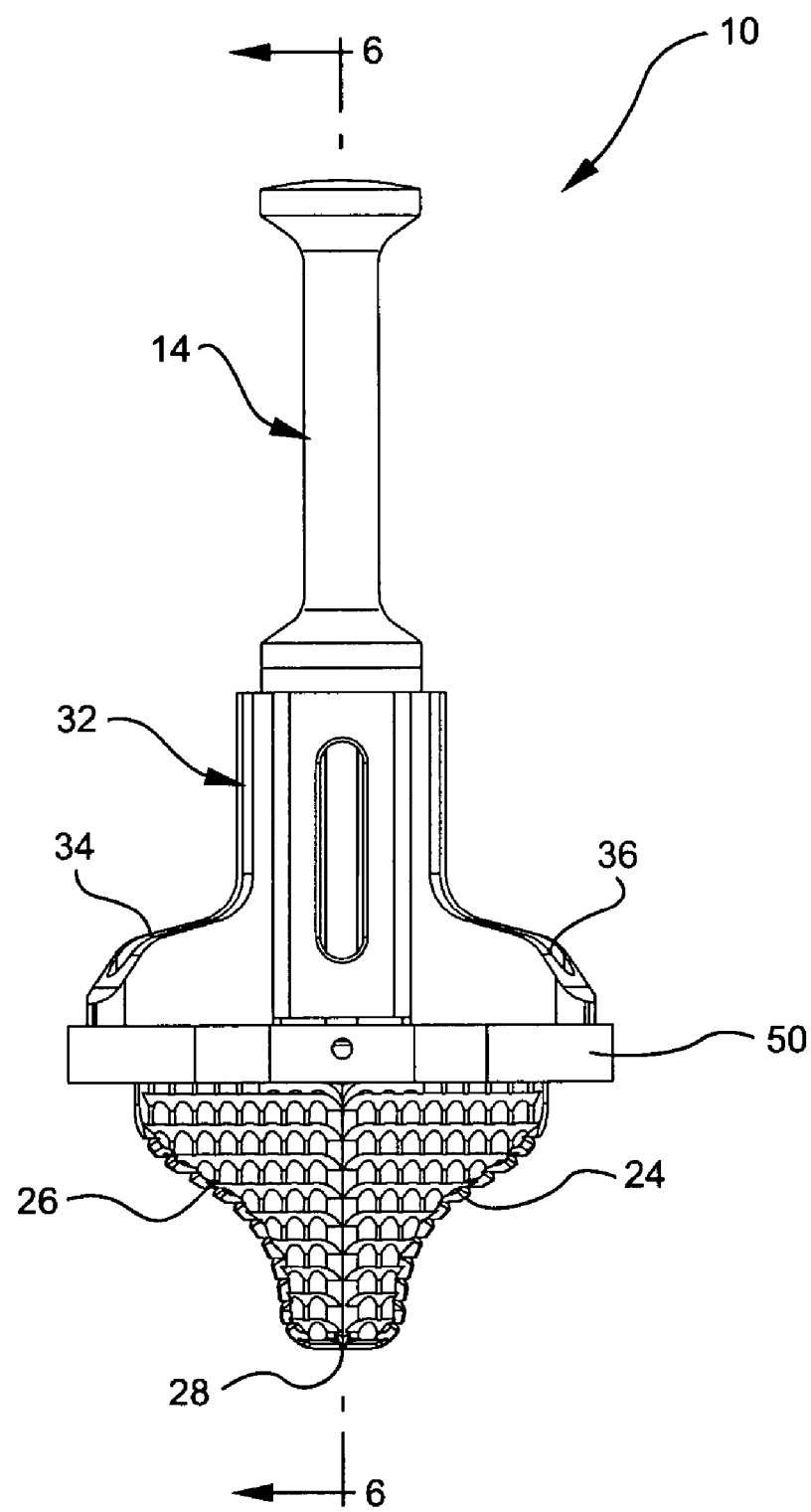
FIG. 4 is a front view of the bone implantation instrument shown in FIG. 3.
Figure 5:
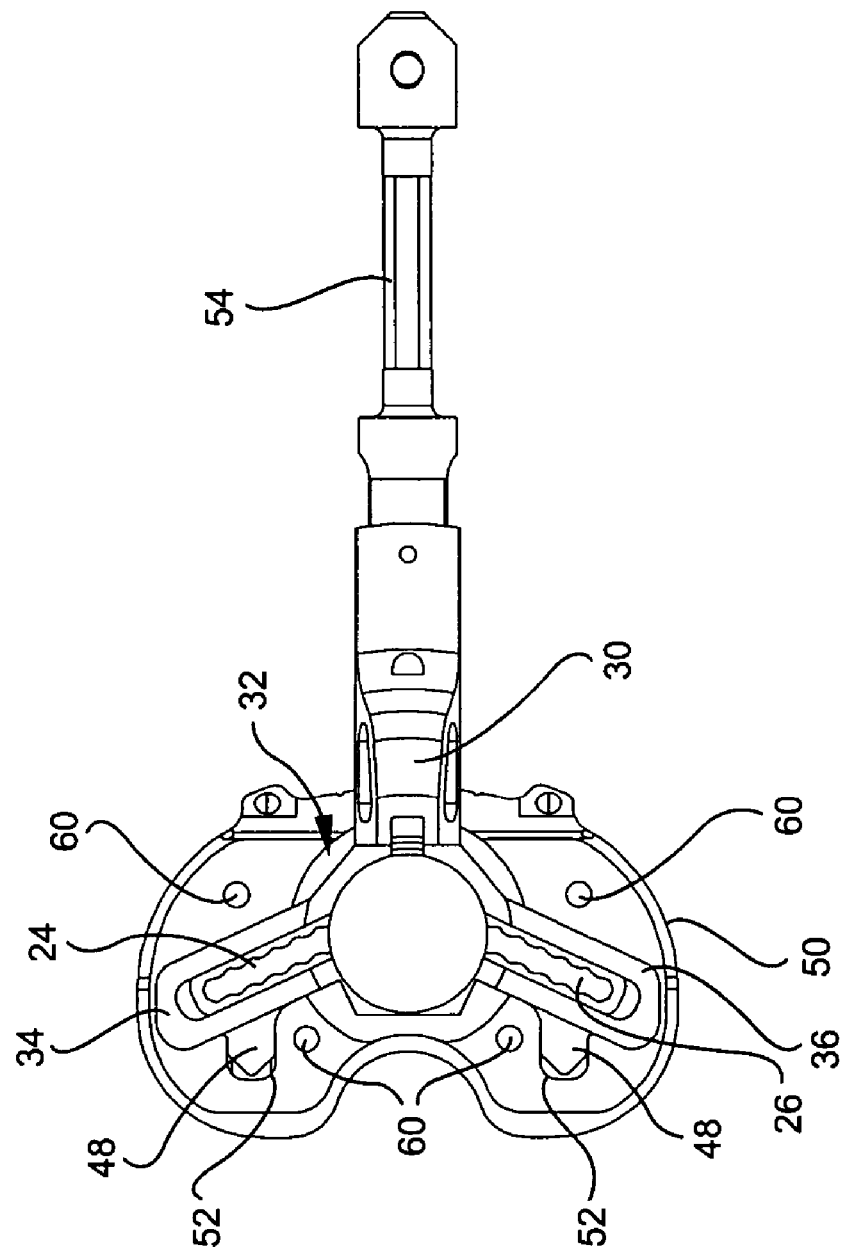
FIG. 5 is a top plan view of the bone implantation instrument shown in FIG. 3.

Before describing several exemplary embodiments of the invention, it is to be understood that the invention is not limited to the details of construction or process steps set forth in the following description. The invention is capable of other embodiments and of being practiced or carried out in various ways.

In overview, one or more embodiments of the invention relates to an implantation instrument and method of forming a recess in a bone. Certain embodiments relate to a punch for forming a recess in a bone, such as a tibia during a knee arthroplasty.

Referring to the drawings and first to FIGS. 1-5, a knee implantation instrument 10 is shown, and in preferred embodiments, an implantation instrument for use in forming a recess in a tibia is shown. According to one or more embodiments, the bone implantation instrument comprises a punch 12 having a proximal portion 14 and a distal portion 16 defining a longitudinal axis 18. According to certain embodiments, the proximal portion 14 of the punch 12 includes a handle, and the distal portion 16 includes a punch tip configured for impaction in a bone. The knee implantation instrument 10 further includes a pivot 22 located between the proximal portion 14 and the distal portion 16 of the punch 12. The pivot 22 preferably permits the proximal portion 14 to be rotated about the pivot 22 and to be moved at an angle with respect to the longitudinal axis 18.

The distal portion 16 of the punch 12 is configured to be advanced into a bone such as a tibia during a knee surgery according to known procedures. The distal portion 16 of the punch 12 is preferably keel or fin shaped in cross section so as to form a fin or keel shaped recess in the bone when it is advanced into a bone. The keel or fin shape on the distal portion 16 of the punch 12 includes a pair of fins 24, 26 and a central keel 28. According to one or more embodiments, the instrument includes a fulcrum 30 configured to cooperate with the proximal portion 14 of the punch 12 when the proximal portion 14 is rotated about the pivot 22 to extract the distal portion 16 of the punch 12 from the bone. As will be described in more detail below, the pivot 22, the proximal portion 14 and the fulcrum 30 cooperate to provide a lever to permit the punch to be extracted from a bone by prying force. According to certain embodiments, the fulcrum 30 includes a raised surface associated with or adjacent the guide member 32.

In one or more preferred embodiments the implantation instrument 10 also includes a guide member 32 configured to direct the distal portion 16 of the punch into the bone. The guide member 32 is preferably elongate and has a pair of fin guides 34, 36 that are configured to direct the fins 24, 26 of the punch 12. According to certain embodiments, the pivot 22 comprises a slot 38 associated with the proximal portion 14 of the punch 12 and a pin 40 associated with the distal portion 16 of the punch 12. Preferably, the slot 38 is elongated and includes an advancement position 37 and retraction position 39.

To prevent rotation of the proximal portion 14 as the punch is advanced into the bone, punch 12 includes a locking member 42. The locking member 42 can include any suitable means for preventing the proximal portion 14 of the punch 12 from inadvertently rotating about the pivot 22, particularly when the punch is being advanced into the bone. In the embodiment shown in FIGS. 1-5, the locking member 42 includes raised stops that cooperate with an abutment surface 44 on the punch 12.

According to one or more embodiments, the guide 32 includes at least engagement element 48 for securing the guide to a punch template 50 attached with the bone. The engagement element may include prongs extending from the guide 32 that engage recesses 52 in the template 50. A handle 54 that is preferably retractable from the guide 32 may also include a projection 56 that cooperates with a mating surface 58 on the template 50. The handle 54 can either be permanently associated with the guide 32 or it may be removable as shown in FIG. 1. The template 50 is typically attached to the bone using fixation pins (not shown) inserted through pin openings 60 on the template 50.

Other embodiments of the invention relate to a method of forming a recess in a bone using a punch and/or extracting a punch from a bone. According to one or more embodiments, the method comprises extracting a keel or fin punch from a bone using prying force.

Figure 6:
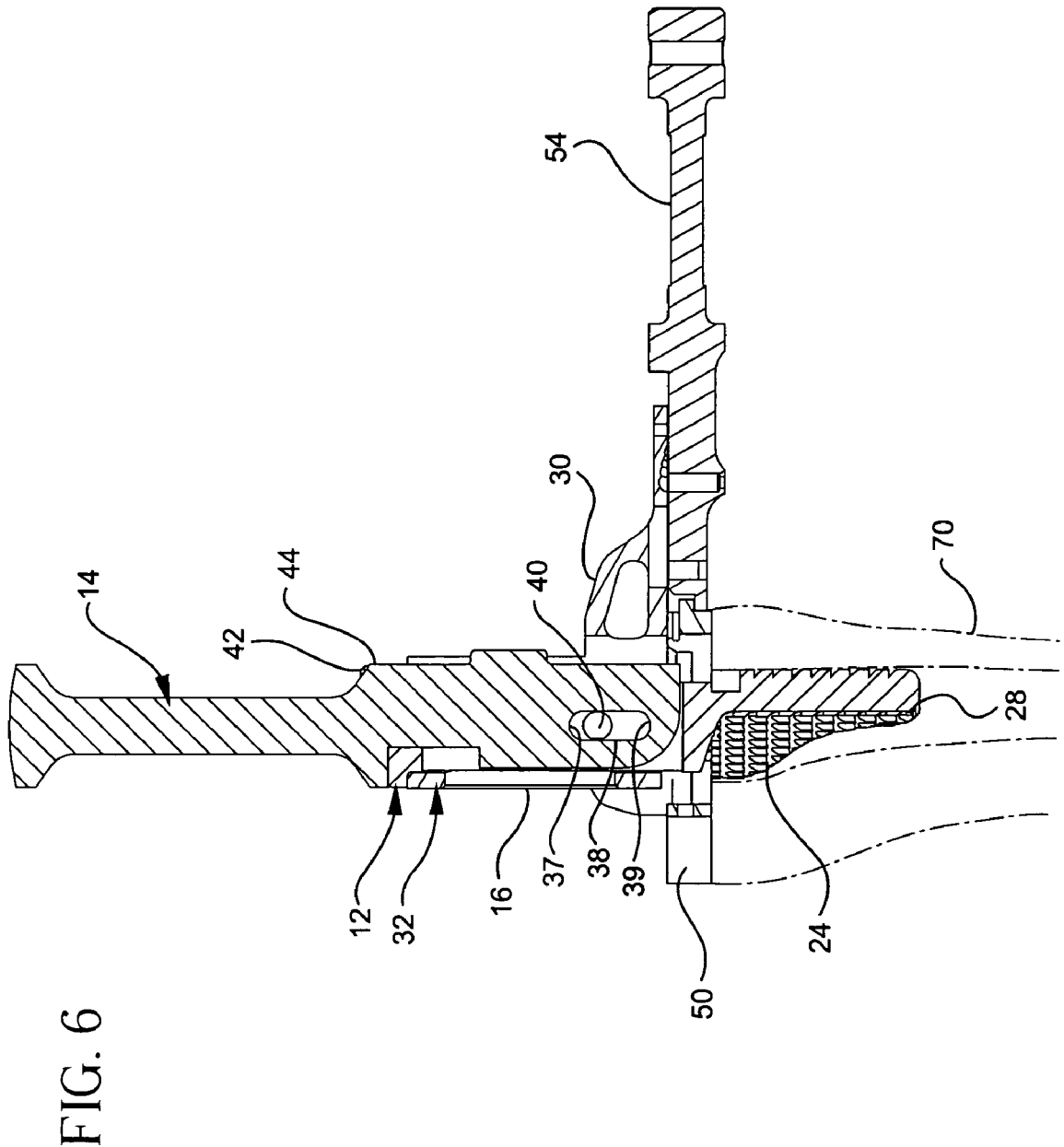
FIG. 6 is a cross-sectional view taken along line 6-6 of FIG. 4 with the punch in the implanted into a bone according to one embodiment.

According to one or more embodiments, a method of forming a recess in a bone and a method of using a knee implantation instrument are provided. According to one or more method embodiments, after choosing an appropriately sized template 50 and fixing the template to the tibia 70 using pins or other suitable fixation means, the practitioner secures the punch guide 32 to the template 50. The punch is inserted into the punch guide as shown in FIG. 6 with the central punch entering the central punch guide and the left and right fins entering the left and right fin guides. The proximal portion 14 of the punch is aligned with the longitudinal axis of the distal portion 16 of the punch. The pin 40 is in the advancement position 37, and the locking member 42 maintains the proximal portion 14 of the punch in position while the punch is being driven into a bone. With the distal portion 16 of the punch in the guide 32, the proximal end 14 of the punch is struck with a mallet or other impaction device so that the distal end of the punch is driven into a section of bone, such as a tibial plateau. The punch is then removed from the bone without the use of a slap hammer, and in a controlled manner as described below according to one or more embodiments. Thereafter, a tibial implant having a shaft corresponding in cross section to the distal end of the keel punch is inserted and cemented in the opening formed by the punch.

Figure 7:
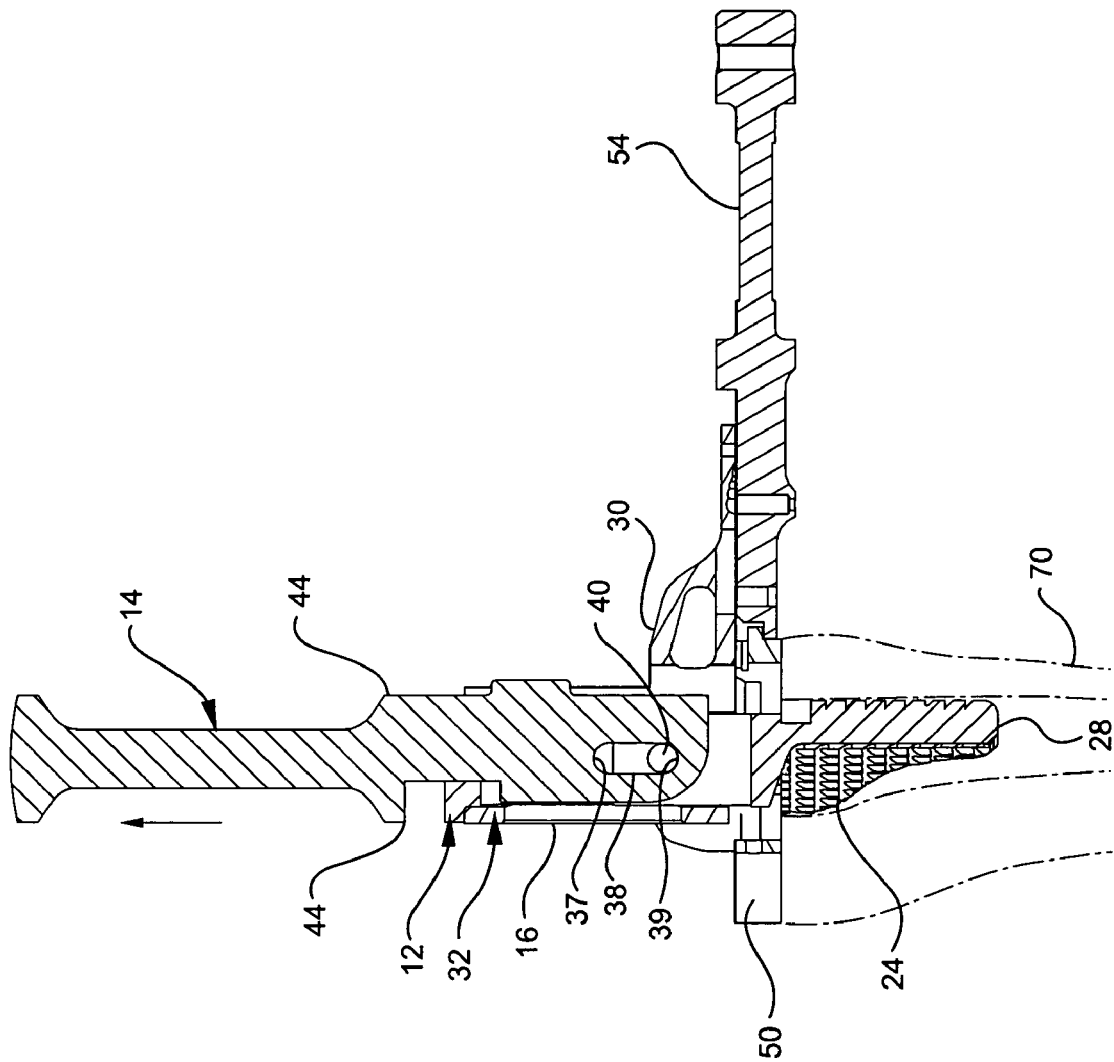
FIG. 7 is a cross-sectional view taken along line 6-6 of FIG. 4 with the proximal portion of the punch in an intermediate position prior to extraction of the distal portion of the punch from a bone.
Figure 8:
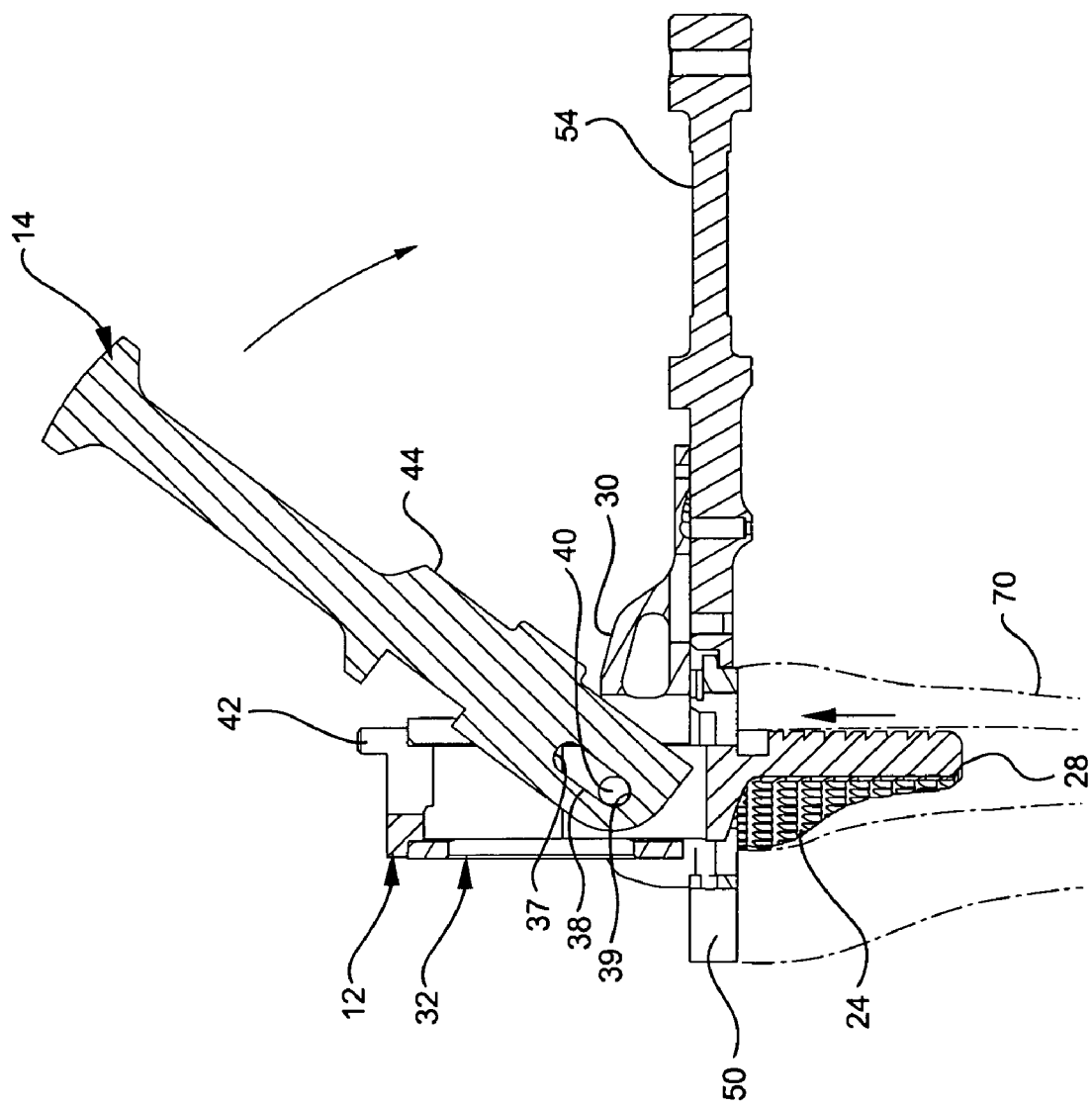
FIG. 8 is a cross-sectional view taken along line 6-6 of FIG. 4 with the proximal portion of the punch a partially extended position during extraction of the distal portion of the punch from a bone.
Figure 9:
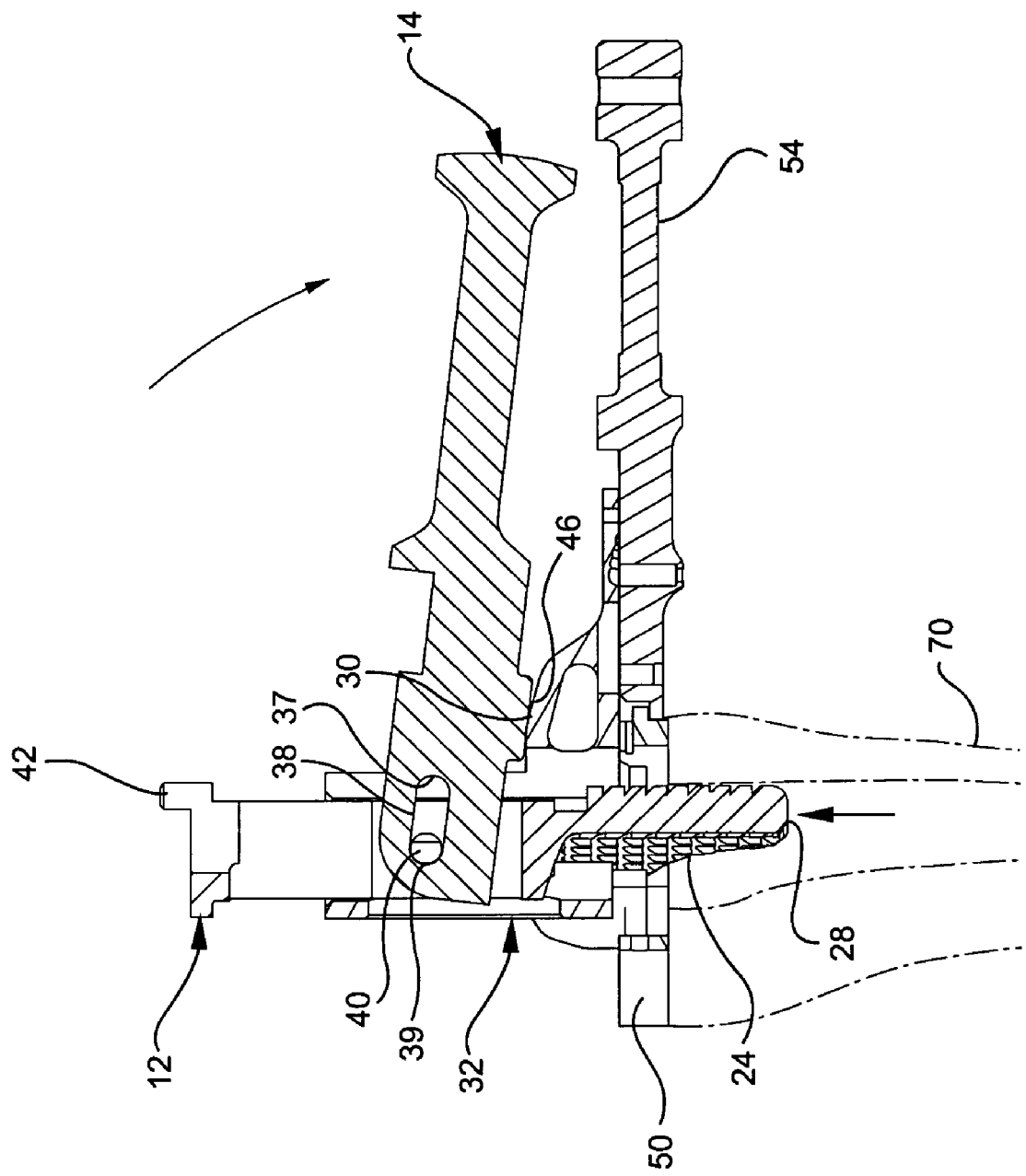
FIG. 9 is a cross-sectional view taken along line 6-6 of FIG. 4 with the proximal portion of the punch a fully extended position after extraction of the distal portion of the punch from a bone.

According to one or more embodiments, a method of extracting a punch from a bone during a surgery such as a knee arthroplasty comprises providing a punch having a handle portion, an impaction tip, a longitudinal axis and a pivot along the longitudinal axis and rotating the handle about the pivot to extract the punch from the bone. Referring to FIG. 7, first the punch handle or proximal portion is lifted into the retraction position 39 so that the punch handle on the proximal portion 14 can be rotated about the pivot 22 as shown in FIGS. 8 and 9. As shown in FIGS. 8 and 9, a portion of the handle is supported by a fulcrum during rotation of the proximal portion of the punch and extraction of the punch from the bone. Thus the proximal portion of the punch is fully extracted from the bone by using a lever formed by a portion of the punch as shown in FIGS. 8 and 9.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims and their equivalents.

What is claimed is:

1. A bone implantation instrument comprising:
    a punch having a distal end with a bone cutting tool thereon and a proximal end and a longitudinal axis, the punch including a pivot pin;
    a guide for guiding the punch into a bone during advancement of the punch, the guide having a fulcrum thereon; and
    a lever, including a proximal portion having an impaction surface thereon and a distal portion having a slot and a guide fulcrum contacting portion, the lever being rotatably affixed to the punch by the pivot pin engaging the slot and aligned with the punch longitudinal axis in a first rotational position, and the slot in the distal lever portion having a proximal portion and a distal end such that when the lever proximal portion is in alignment with the punch longitudinal axis during advancement of the punch the pivot pin is in the proximal portion of the slot and when the lever is angled with respect to the punch longitudinal axis during extraction of the punch from the bone the guide fulcrum contacts the lever fulcrum contacting portion and the pivot pin contacts the distal end of the slot.

2. The bone implantation instrument of claim 1, further comprising a punch template mounted on the bone for receiving the guide.

3. The bone implantation instrument of claim 2, wherein the guide includes a handle.

4. The bone implantation instrument of claim 3, wherein the punch is adapted to be used in a knee surgery.

5. A bone implantation instrument comprising:
    a guide with a fulcrum thereon
    a punch having a bone cutting tool thereon being guided by the guide and having a longitudinal axis, the punch having a pivot pin thereon:
    an impaction lever extending along a longitudinal axis rotatably mounted on the punch for impacting the punch, the impaction lever having a first end contacting an impaction surface on the punch and a second end for contacting an impaction tool, the impaction lever having a slot thereon for slidably receiving the pivot pin, the pivot pin being located in an advancement position within the slot at a slot position closer to the impaction lever second end when the first lever end is contacting the punch impaction surface and the pivot pin being located in a retraction position within the slot when the impaction lever is rotated so that the longitudinal axis thereof is at an angle to the longitudinal axis of the punch, the impaction lever having a surface that contacts the fulcrum of the guide upon the rotation of the impaction lever with respect to the punch, the pivot pin adjacent an end of the slot closer to the impaction lever first end when the impaction lever surface contacts the fulcrum of the guide.

6. The bone implantation instrument of claim 5, wherein the punch includes a locking member to prevent rotation of the proximal portion as the cutting tool is advanced into the bone.

7. The bone implantation instrument of claim 5, wherein the guide fulcrum includes a raised surface for contacting the lever fulcrum contacting portion.

8. The bone implantation instrument of claim 7, wherein the guide includes an engagement element for securing the guide to a punch template associated with the bone.

9. The bone implantation instrument of claim 8, wherein the guide further includes a handle.

10. The bone implantation instrument of claim 9, wherein the cutting tool is generally keel-shaped in cross section.

11. The bone implantation instrument of claim 10, wherein the bone cutting tool adapted to be used in a knee surgery.

* * * * *

UNITED STATES PATENT AND TRADEMARK OFFICE
CERTIFICATE OF CORRECTION

PATENT NO. : 7,390,327 B2  Page 1 of 1
APPLICATION NO. : 10/678351
DATED : June 24, 2008
INVENTOR(S) : Carlos E. Collazo and Scott Logan It is certified that error appears in the above-identified patent and that said Letters Patent is hereby corrected as shown below:

Column 6, line 62, after "cutting tool" insert --is--.

Signed and Sealed this

Twenty-seventh Day of October, 2009

David J. Kappos
*Director of the United States Patent and Trademark Office*